United States Patent
Schmidt et al.

(10) Patent No.: US 9,687,206 B2
(45) Date of Patent: Jun. 27, 2017

(54) METHOD AND CT SYSTEM FOR TOPOGRAM SCANNING

(71) Applicant: Siemens Aktiengesellschaft, Munich (DE)

(72) Inventors: Bernhard Schmidt, Fuerth (DE); Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 260 days.

(21) Appl. No.: 14/520,400

(22) Filed: Oct. 22, 2014

(65) Prior Publication Data

US 2015/0124928 A1 May 7, 2015

(30) Foreign Application Priority Data

Nov. 5, 2013 (DE) .......................... 10 2013 222 386

(51) Int. Cl.
  *A61B 6/00* (2006.01)
  *A61B 6/03* (2006.01)
  *A61B 6/02* (2006.01)

(52) U.S. Cl.
  CPC ............ *A61B 6/5223* (2013.01); *A61B 6/025* (2013.01); *A61B 6/032* (2013.01); *A61B 6/4021* (2013.01); *A61B 6/4266* (2013.01); *A61B 6/5205* (2013.01)

(58) Field of Classification Search
  CPC ........ A61B 6/025; A61B 6/032; A61B 6/5223
  See application file for complete search history.

(56) References Cited

U.S. PATENT DOCUMENTS

| 5,060,246 A | 10/1991 | Van Der Brug et al. |
| 2004/0101095 A1 | 5/2004 | Jing et al. |

(Continued)

FOREIGN PATENT DOCUMENTS

| DE | 102006051147 A1 | 5/2008 |
| WO | WO-2004049949 A1 | 6/2004 |

OTHER PUBLICATIONS

J. Dobbins IIII, "Chest tomosynthesis; Technical principles and clinical update", European Journal of Radiology 72 (2009), 21 pgs; 2009.

(Continued)

*Primary Examiner* — Dani Fox
(74) *Attorney, Agent, or Firm* — Harness, Dickey & Pierce, P.L.C.

(57) ABSTRACT

A method for improved utilization of a radiation dose applied to an examination object during topogram scanning of a CT system, and a CT system with a system axis using a cylindrical curved multi-row detector, are disclosed. In an embodiment, the method includes topogram scanning of the examination object with at least one emitter-detector combination disposed on a rotatable gantry from a predetermined rotation angle of the gantry, wherein during the topogram scanning a relative movement occurs between examination object and emitter-detector combination in the system axis direction; calculation of at least one flat image in at least two planes running in parallel to the system axis in each case by a tomosynthesis reconstruction; and storage and/or further processing of at least one of the flat images of the examination object to represent a topogram.

22 Claims, 3 Drawing Sheets

(56) References Cited

U.S. PATENT DOCUMENTS

2008/0123801 A1* 5/2008 Flohr .................... A61B 6/032
  378/4
2008/0298539 A1* 12/2008 Nakanishi .............. A61B 6/032
  378/15

OTHER PUBLICATIONS

J. Dobbins III, "Tomosynthesis imaging: At a translational crossroads", Med. Phys. 36 (6), Jun. 2009, 12 pgs, 2009 Am. Assoc. Phys. Med.
M. Maisl, "Computerlaminographie, Grundlagen und technische Umsetzung", 6 pgs, Saarbrücken, Deutschland.
Office Action for Chinese Patent Application No. 201410602283.7 issued on Nov. 15, 2016 and English translation thereof.

* cited by examiner

FIG 3
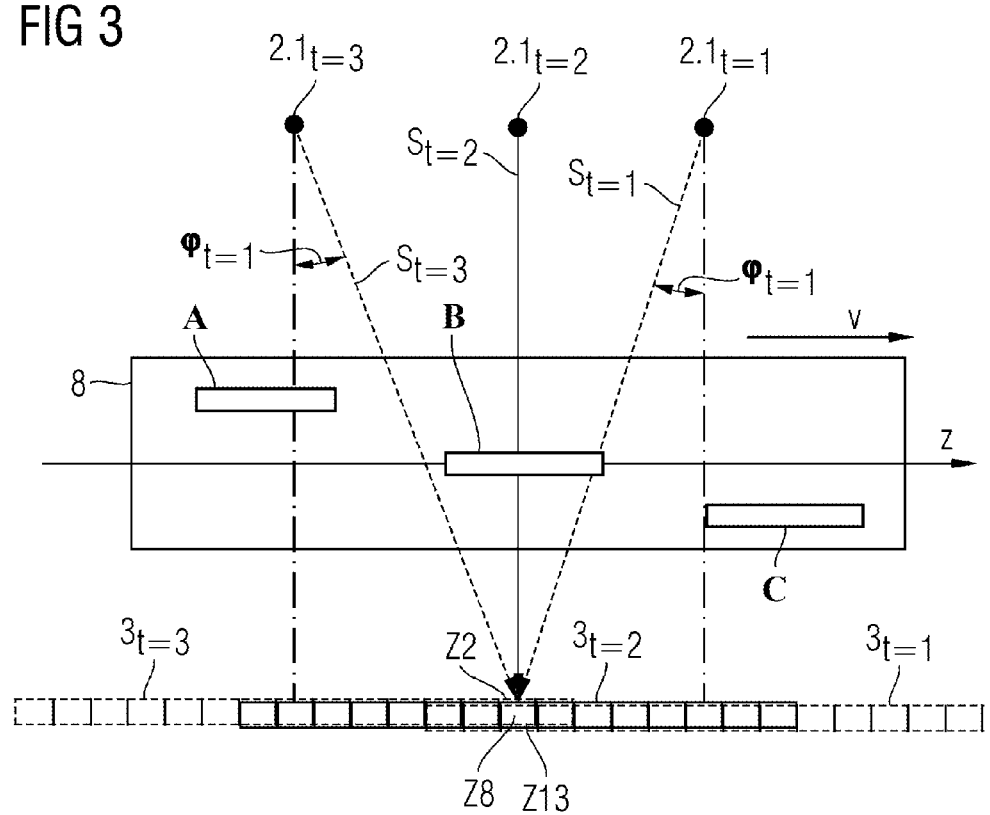
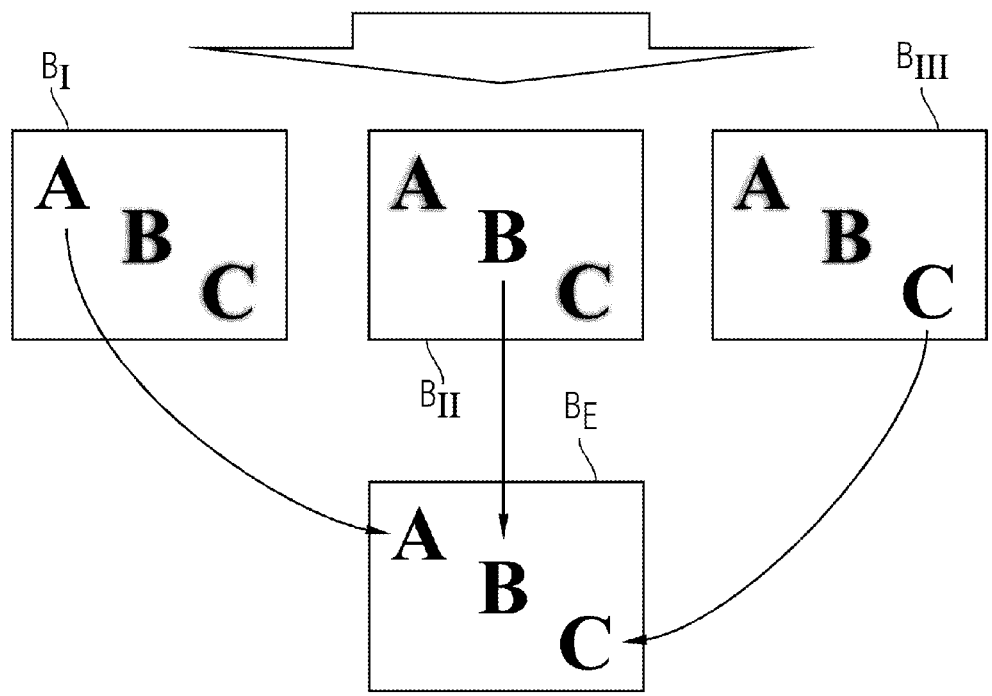

METHOD AND CT SYSTEM FOR TOPOGRAM SCANNING

PRIORITY STATEMENT

The present application hereby claims priority under 35 U.S.C. §119 to German patent application number DE 102013222386.2 filed Nov. 5, 2013, the entire contents of which are hereby incorporated herein by reference.

FIELD

At least one embodiment of the invention generally relates to a method for improved utilization of a radiation dose applied to an examination object during topogram scanning of a CT system with a system axis using a cylindrical curved multi-row detector and/or a CT system with program code for carrying out this method.

BACKGROUND

Methods for carrying out a topogram scan with a CT system using a cylindrical the curved multi-row detector and corresponding CT systems with program code for carrying out this method are generally known.

Such topogram scans mostly serve for planning recording of CT images. If multi-row detectors, i.e. detectors relatively wide in the system axis direction or also the z-direction are used for scanning a topogram, then multiple information at the same z-position in each case occurs during the scanning because of the wide radiation cone beam which is moved over the examination object—always related to the same beam angle in the circumferential direction, wherein however the rays which create this absorption information multiple times at the same z-position of the examination object do not always pass through the identical tissue, since they each have different angles of inclination. In practice however all absorption information which is measured at the same z-position of the examination object is used for imaging as if it penetrated identical voxels in the examination object and added them up overall for the image information.

In this way such topograms have the disadvantage that the images produced are unsharp and in addition that no overlay-free representation is undertaken and thus no depth information is also presented which would make possible a localization, of a lesion for example, in the depth.

SUMMARY

At least one embodiment of the invention is directed to an improved method and an improved CT system in which in each case a sharper image can be created and the opportunity is also provided for outputting depth information relating to the parts represented in the examination object.

Advantageous developments of the invention are the subject matter of dependent claims.

Accordingly, the inventors propose an embodiment of a method for improved utilization of a radiation dose applied to an examination object during topogram scanning of a CT system with a system axis using a cylindrical curved multi-row detector, having the following method steps:

Topogram scanning of the examination object with at least one emitter-detector combination disposed on a rotatable gantry from a predetermined angle of rotation of the gantry, wherein during the topogram scanning a relative displacement takes place between examination object and emitter-detector combination in the system axis direction, Computation of at least one flat image in the at least two planes running parallel to the system axis in each case by a tomosynthesis reconstruction (=laminography reconstruction), and Storage and/or further processing of at least one of the flat images of the examination object to represent a topogram.

As well is the embodiments of the inventive method, the inventors also propose an embodiment of a CT system having at least one emitter-detector combination disposed on a gantry and a control and processing unit with a memory for program code, wherein the program code emulates at least one embodiment of the inventive method described above.

BRIEF DESCRIPTION OF THE DRAWINGS

The invention is described below in greater detail with the aid of the figures, wherein only the features needed for understanding the invention are shown. The following reference characters are used: 1: CT system; 2: X-ray tube; 2.1: Focus; 3: Detector; 4: Gantry housing; 5: Patient couch; 7: System axis; 8: Patient/Examination object; 9: Control and processing unit; A, B, C: Structures; BE: Result image; BP: Projection image; BI, BII, BIII: Slice images of planes I, II, III; M: Central ray; Prg1-Prgn: Program code; v: Speed of advance; S: Rays; t: Time; Z: Detector element; $\phi$: Cone beam angle.

In the individual figures:

FIG. 3: shows a section along the z axis of the CT system with the emitter-detector system shown schematically at three points in time during topogram scanning.

DETAILED DESCRIPTION OF THE EXAMPLE EMBODIMENTS

Figure 1:
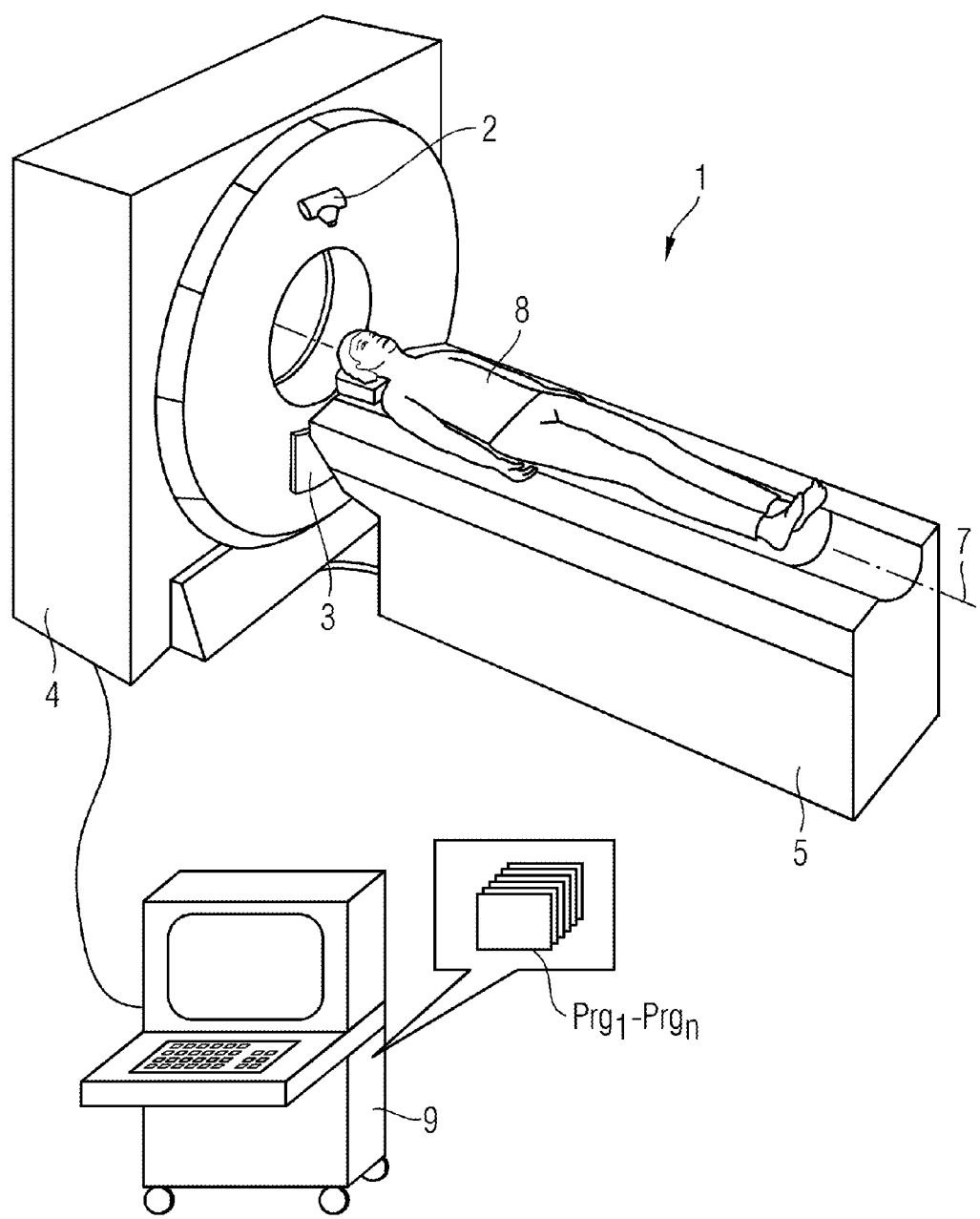
FIG. 1: shows a CT system with control and processing unit for carrying out an embodiment of the inventive method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors have recognized that the disadvantages of topogram scanning described above can be avoided if, during the recording of the topogram, the information about the slant of the respective scanning beam is processed as well and the height information is incorporated into the graphical presentation by a tomosynthesis reconstruction or also computer laminography reconstruction. In addition the distortion of the graphical representation can also be corrected.

In the current usual acquisition of the topogram the scanning is undertaken by setting a fixed angular position, AP (anterior-posterior) or lateral, the rotation of the emitter-detector system is thus halted. Subsequently, while setting a continuous radiation of the x-ray tubes, the table with the patient is moved into the gantry opening. In this case small collimations, e.g. 6×0.6 mm, are normally selected in order to take account of the geometrical effects and to prevent artifact formation. Normally higher table speeds are also selected, e.g. 100 mm/s, in order to reduce the possibility of movement artifacts.

Through the continuous radiation, the short integration times, the continuous table advance and the fixed position of the emitter-detector system a drastic overscanning in the z-direction and thus, as a result of the different irradiation angle of the scanning rays, additional information which has previously not been utilized is obtained. Current topograms are interpolated to an edge length of 1 mm×1 mm, wherein the original resolution is lost.

It is therefore proposed that topogram acquisition continue to be executed with a fixed emitter-detector system, wherein preferably a maximum possible collimation is set (e.g. 128×0.6 mm). The table advance speed can be further increased in such cases (e.g. 200 mm/s). The oblique rays in the z-direction in this case allow additional information to be obtained here, since radiation passes through pixels multiple times and therefore deliver information which can be used for calculating the depth information.

In order to improve the quality, especially in relation to the resolution, of the topogram, a tube-side modulation of the focus can be switched on as spring focus. This can increase the resolution in the $\phi$ direction, i.e. the direction of rotation of the gantry or the row direction of the detector as well as in the z-direction, depending on the capabilities of the system used.

In order to further improve the resolution of the topogram, a UHR comb (UHR=ultra high resolution) can be moved over the detector. The UHR comb serves to cover the detector channels mechanically in the $\phi$ and/or z-direction and thus reduce the active surface of the detector pixel.

Subsequently the height position of the individual planes can be computed from the recorded data by tomosynthesis reconstruction. This depth information can then be used in order to correct projective distortion.

An embodiment of the method also has the advantage of being able to be used with all conventional CT systems with wide detectors and of only a corresponding software adaptation being needed to allow this to be done, wherein it is basically true to say that the method works all the better, the broader the detector used is in the z-direction.

As regards the generally-known tomosynthesis reconstruction, also known as computer laminography reconstruction, the reader is referred by way of example to the (German language) publication from 2010 entitled "Computerlaminographie, Grundlagen and technische Umsetzung" by Michael Maisl, Christian Schorr, Felix Porsch and Ulf Hassler, able to be viewed at http://www.yumpu.com/de/document/view/9781863/computerlaminographie-grundlagen-und-technische-ndtnet.

Accordingly, the inventors propose an embodiment of a method for improved utilization of a radiation dose applied to an examination object during topogram scanning of a CT system with a system axis using a cylindrical curved multi-row detector, having the following method steps:

Topogram scanning of the examination object with at least one emitter-detector combination disposed on a rotatable gantry from a predetermined angle of rotation of the gantry, wherein during the topogram scanning a relative displacement takes place between examination object and emitter-detector combination in the system axis direction, Computation of at least one flat image in the at least two planes running parallel to the system axis in each case by a tomosynthesis reconstruction (=laminography reconstruction), and Storage and/or further processing of at least one of the flat images of the examination object to represent a topogram.

Through this embodiment of the method, in which the absorption information obtained in the topogram scanning from different rays running obliquely through the examination object is used in order, with the aid of a tomosynthesis reconstruction, to obtain depth information from the examination object, the result now achieved is that absorption information previously deemed to be redundant is evaluated as regards its additional information content. This means that it is possible to determine the position of individual structures in the examination object significantly more precisely and also to represent them in improved-quality images.

It is also useful if, before the tomosynthesis reconstruction, the measured cylindrical projections are converted into flat projections. This enables reconstruction algorithms to be used which were previously used in tomosynthesis reconstructions with flat detectors, for example in mammography.

Furthermore it is advantageous for a detector-side collimator to be used for topogram scanning, which restricts the rays in the direction of the system axis and/or in the rotation direction of the gantry (=circumferential direction). Thus on the one hand radiation scattering effects are reduced and on the other hand an improved imaging resolution is achieved.

To present the topogram a single flat image in a predetermined slice plane in the examination object can optionally be displayed or a number of flat images in a number of slice planes in the examination object can be displayed overlaid.

As regards this proposed overlaying, it should be pointed out that such overlaying cannot only take place in a simple manner in a number of planes, but that also individual structures or image parts from different image planes can be sought here in accordance with image quality criteria and combined into one combination producing an optimum image quality.

Basically an x-ray tube which forms a single locally-fixed focus relative to the x-ray tube can be used as an emitter. To improve the imaging power however an x-ray tube can also be used as the emitter which forms a spring focus. The spring focus here can in a known way assume two different positions during the scanning relative to the x-ray tube in the system axis direction or in the circumferential direction in each case.

It is further especially advantageous to use a multi-row detector with more than the 6 rows, preferably a 64-row detector or 128-row detector, since as a rule a higher number of rows leads to a greater width of the detector in the z-direction and thus to a greater angular range (overall taper angle) of the scanning rays to the z axis.

Accordingly it is also proposed that the emitter-detector geometry should be designed so that a preponderant number of the rays used for scanning are emitted with a taper angle greater than 3°.

As well is the embodiments of the inventive method, the inventors also propose an embodiment of a CT system having at least one emitter-detector combination disposed on a gantry and a control and processing unit with a memory for program code, wherein the program code emulates at least one embodiment of the inventive method described above.

FIG. 1 shows a typical CT system 1 in a 3*d* representation with a gantry housing 4 in which an emitter-detector system is disposed on a gantry not shown in any greater detail. The emitter-detector system essentially consists of the x-ray tube 2 in which a focus is created, emanating from which a cone-shaped ray bundle is directed onto the opposite multi-row detector 3. For topogram scanning the emitter-detector system 2, 3, otherwise able to be rotated with the gantry, is held in a predetermined angular position, while the object to be examined, here a patient 8, is pushed continuously with the aid of a movable patient couch 5 along the system axis (=z-axis) 7 through the measurement field. During the movement of the patient 8 along the system axis 7 the emitter-detector system 2, 3 is in operation, so that a plurality of projections are taken from the same projection angle. Since the detector 3 has many detector rows, detector rows which are at the identical z-position of the examination object are read out multiple times during the scan. In the prior art this multiple scanning information at the same in z-position—and of course also in the same column of the detector—obtained in this way is combined into one image pixel in the topogram.

In accordance with an embodiment of the invention however account is now taken of the fact that, during their passage through the examination object during the topogram scanning, the different detector rows passing the same z-position of the examination object after one another are each struck by rays with different inclination to the z-axis and thus also pass through different parts of the examination object. To this end, with the aid of the projections determined during the topogram scan, a computer laminography reconstruction is carried out so that a number of slice images are produced which are disposed in parallel to the z-axis and preferably at right angles to the central beam between the emitter 2 and detector 3.

The execution sequence of the scanning and the execution of the reconstruction is performed by the control and processing unit 9 which has corresponding program code Prg1-Prgn in its memory, which is executed during operation.

To illustrate an embodiment of the inventive method, FIGS. 2 and 3 again show the emitter-detector system from FIG. 1 schematically in a longitudinal section along the system axis and along the central ray M between the emitter and detector. The detector 3 typically has 16 detector rows here, wherein four individual rays between the focus 2.1 of the emitter and the detector 3 are shown explicitly. For scanning the examination object 8 is pushed, with the gantry not rotating, at a speed of advance v along the z-axis through the beam path of the emitter-detector system and when this is done—as is also the case with orbital scanning—simultaneously a plurality of readouts are undertaken at the detector elements of the detector. As a result of the width of the detector 3 the examination object 8 is penetrated multiple times at the same z-position of the detector elements or detector rows—relative to the examination object 8—so that each ray and thus each measurement relates to rays with different inclination angles. Accordingly each ray also represents a different path through the examination object 8.

In FIG. 3, to illustrate this process, the section through the emitter-detector system depicted in FIG. 2 is shown once again, however three situations offset in time are shown. According to the displayed speed of advance v of the examination object 8 from left to right, the scanning situation initially corresponds to the focus detector combination 2.1t=1, 3t=1 shown by dashed lines on the right with the ray St=1 shown at time t=1. This ray St=1 strikes the selected z-position of the examination object at the 13th detector element Z13 of the shown column of the detector 3. The advance proceeds with constant measurements until the examination object 8 with this z-position has reached the position of the detector 3 at which the ray St=2 strikes the detector element Z8 at right angles. This situation corresponds to the focus-detector combination 2.1t=2, 3t=2 shown by a solid line with perpendicular ray St=2. After further advance, a measurement is also taken in the situation of the focus-detector combination 2.1t=3, 3t=3, again shown by a dashed line, with the opposingly-angled ray St=3, which strikes the detector element Z2.

Figure 2:
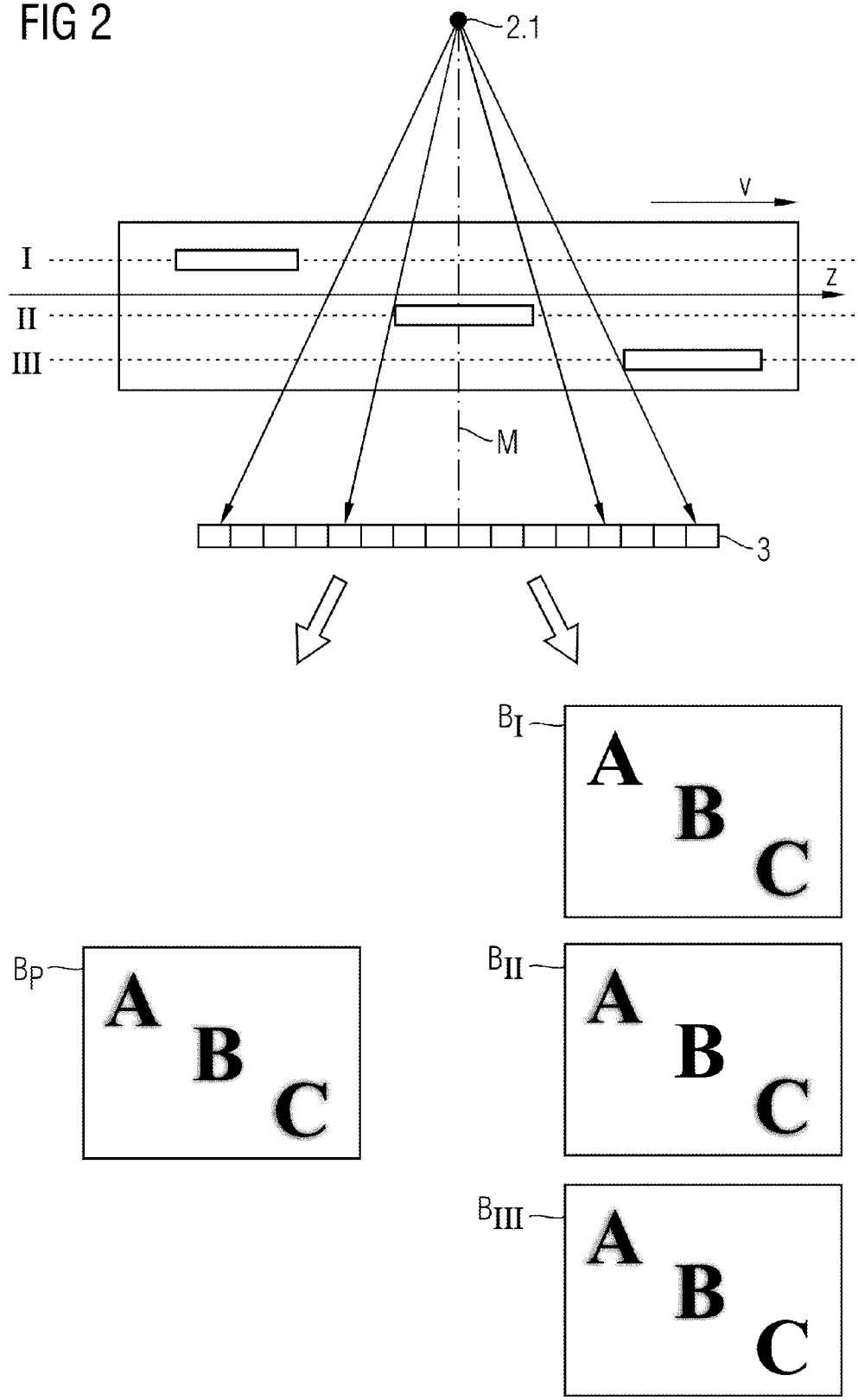
FIG. 2: shows a section along the z axis of the CT system with the emitter-detector system shown schematically.

As is not difficult to see, all of the rays St=1 to St=3,— which are certainly shown here at an exaggerated angle— with the taper angles ϕt=1 to ϕt=3 create different absorption values, since they penetrate the examination object 8 on different paths. Despite this in the prior art these values are used for describing the radiation absorption at the same z-position so that an unsharp projection image BP is produced, as is shown in FIG. 2. In accordance with the invention however the absorption information now measured at different oblique taper angles is incorporated into a laminography reconstruction so that now a number of slice images can be reconstructed in the z axis. Such reconstructed slice images BI to BIII for the planes I to III in the examination object are shown in FIG. 2, wherein accordingly the structures A, B and C, which are located in the planes I to III will be shown with different degrees of sharpness depending on the selected reconstruction plane. In the laminography reconstructed slice image BI, which represents the plane I, the structure A, in slice image BII the structure B and in slice image BIII the structure C are therefore shown especially sharp, while the other structures in each case, depending on their distance from the image plane, fade further into the background. The dashed-line representation shown can only reproduce this inadequately.

In accordance with an embodiment of the invention is now possible on the one hand for the user to determine the position of the structures in the examination object in relation to their assignment to a particular plane and on the other hand to select or to create improved imaging by this method. This can for example also be done through an area-specific weighted overlaying of the individual plane images, as is shown by way of example in FIG. 3 with the result image BE.

Although the invention has been illustrated in more detail and described by the preferred example embodiments, the invention is not restricted by the disclosed examples and other variations can be derived therefrom by the person skilled in the art without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for improved utilization of a radiation dose applied to an examination object during topogram scanning of a CT system with a system axis using a cylindrical curved multi-row detector, comprising:
    topogram scanning of the examination object with at least one emitter-detector combination disposed on a rotatable gantry from a rotation angle of the gantry, wherein during the topogram scanning a relative movement takes place between examination object and emitter-detector combination in the system axis direction;
    calculating at least one flat image, in at least two respective planes running in parallel to the system axis, by a tomosynthesis reconstruction; and
    at least one of storing and further processing at least one of the flat images of the examination object to represent a topogram.

2. The method of claim 1, further comprising:
    converting measured cylindrical projections of the cylindrical curved multi-row detector, before the tomosynthesis reconstruction, into flat projections.

3. The method of claim 1, wherein a detector-side collimator, configured to restrict the rays at least in the direction of the system axis, is used for the topogram scanning.

4. The method of claim 1, wherein a detector-side collimator, configured to which restrict the rays at least in the direction of rotation of the gantry, is used for topogram scanning.

5. The method of claim 1, wherein, to represent the topogram, a single flat image is displayed in a slice plane in the examination object.

6. The method of claim 1, wherein, to represent the topogram, a number of flat images in a number of slice planes in the examination object are displayed overlaid.

7. The method of claim 1, wherein an x-ray tube, which forms a single fixed focus relative to the x-ray tube, is used as the emitter.

8. The method of claim 1, wherein an x-ray tube, which forms a spring focus, is used as the emitter.

9. The method of claim 8, wherein the spring focus assumes at least two different positions in the system axis direction relative to the x-ray tube during the scanning.

10. The method of claim 8, wherein the spring focus assumes at least two different positions in the circumferential direction relative to the x-ray tube during the scanning.

11. The method of claim 1, wherein a detector with more than six rows is used as the multi-row detector.

12. The method of claim 1, wherein a preponderant number of the rays used for scanning are emitted at a taper angle of greater than 3°.

13. The method of claim 1, further comprising obtaining depth information from the topogram scanning of the examination object.

14. The method of claim 2, wherein a detector-side collimator, configured to restrict the rays at least in the direction of the system axis, is used for the topogram scanning.

15. The method of claim 2, wherein a detector-side collimator, configured to which restrict the rays at least in the direction of rotation of the gantry, is used for topogram scanning.

16. The method of claim 2, wherein, to represent the topogram, a single flat image is displayed in a slice plane in the examination object.

17. The method of claim 2, wherein, to represent the topogram, a number of flat images in a number of slice planes in the examination object are displayed overlaid.

18. The method of claim 2, wherein an x-ray tube, which forms a single fixed focus relative to the x-ray tube, is used as the emitter.

19. The method of claim 2, wherein an x-ray tube, which forms a spring focus, is used as the emitter.

20. The method of claim 11, a 64-row detector is used as the multi-row detector.

21. The method of claim 11, a 128-row detector is used as the multi-row detector.

22. A CT system, comprising:
at least one emitter-detector combination, disposed on a gantry; and
a control and processing unit including a memory for storing program code, the program code being executable during operation to perform at least
topogram scanning of the examination object with at least one emitter-detector combination disposed on a rotatable gantry from a rotation angle of the gantry, wherein during the topogram scanning a relative movement takes place between examination object and emitter-detector combination in the system axis direction;
calculating at least one flat image, in at least two respective planes running in parallel to the system axis, by a tomosynthesis reconstruction; and
at least one of storing and further processing at least one of the flat images of the examination object to represent a topogram.

* * * * *